United States Patent [19]
Johnson et al.

[11] Patent Number: 5,756,550
[45] Date of Patent: May 26, 1998

[54] METHOD OF TREATMENT OF PARKINSON'S DISEASE

[75] Inventors: Peter Johnson, Aspley Guise, England; Barry E. Watkins, Fairport; Eric W. Harris, Rochester, both of N.Y.

[73] Assignee: Astra AB, Sodertalje, Sweden

[21] Appl. No.: 708,500

[22] Filed: Sep. 5, 1996

Related U.S. Application Data

[62] Division of Ser. No. 470,705, Jun. 6, 1995, Pat. No. 5,650,443, which is a continuation of Ser. No. 325,445, Nov. 21, 1994, abandoned.

[30] Foreign Application Priority Data

| May 2, 1992 | [GB] | United Kingdom | 9209599 |
| Apr. 30, 1993 | [WO] | WIPO | PCT/GB93/00908 |

[51] Int. Cl.$^6$ .................................................. A61K 31/165
[52] U.S. Cl. ................................................................ 514/626
[58] Field of Search ............................................... 514/626

[56] References Cited

FOREIGN PATENT DOCUMENTS 0 427 427 A2   5/1991   European Pat. Off.

OTHER PUBLICATIONS

Klockgether et al. "NMDA Antagonists potentiate. . ." Annals of Neurology, vol. 28 No. 4, 1990, pp. 539–546.

R. Griffith et al. "Preclinical Neuroprotective . . ." Abstracts of Papers of the American Chemical Society, vol. 201, No. 1–2, 1991, p. 22.

R.V. Eller et al. "Remacemide and L–Dopa . . ." Soc. Neurosci. Abstract, vol. 18 No. 1–2, 1992, p. 1080.

Remington, Pharmaceutical Sciences, 15th Ed. Mack Pub. Co., 1995, pp. 855–857–858.

*Primary Examiner*—Phyllis G. Spivack
*Attorney, Agent, or Firm*—Nixon & Vanderhye

[57] ABSTRACT

2-Amino-N-(1,2-diphenyl-1-methylethyl) acetamide (remacemide), or a pharmaceutically acceptable salt thereof, for use in the treatment of Parkinson's disease is disclosed.

1 Claim, No Drawings

METHOD OF TREATMENT OF PARKINSON'S DISEASE

This is a Rule 60 Division of application Ser. No. 08/470,705, filed 6 Jun. 1995. U.S. Pat. No. 5,650,443 which is a Rule 62 continuation of application Ser. No. 08/325,445, filed 21 Nov. 1994, now abandoned.

This invention relates to a novel method of treatment of patients suffering from Parkinson's disease, the novel use of a known compound in the treatment of Parkinson's disease, and to pharmaceutical products and formulations for use in that treatment.

Parkinson's disease is thought to be caused by arteriosclerotic changes in the basal ganglia and is characterized by rhythmical muscular tremors and rigidity of movement.

European Patent Application 279937 discloses 2-amino-N-(1,2-diphenyl-1-methylethyl)acetamide (hereinafter referred to as "remacemide") and its pharmaceutically acceptable salts, and their use as anti-epileptic agents. European Patent Application 427427 discloses the use of remacemide and its pharmaceutically acceptable salts in the treatment of neurodegenerative diseases: however, their use in the treatment of Parkinson's disease is not mentioned. Remacemide and its pharmaceutically acceptable salts are thought to be non-competitive N-methyl-D-aspartate (NMDA) antagonists.

3-Hydroxy-L-tyrosine (hereinafter referred to as "L-dopa") is a well known agent for use in the treatment of Parkinson's disease.

The use of NMDA antagonists to potentiate the antiparkinsonian action of L-dopa in monoamine-depleted rats has been disclosed by Klockgether et al (Annals of Neurology, vol 28, No 4, p539, 1990).

It has now been found that administration of remacemide, or a pharmaceutically acceptable salt thereof, in conjunction with L-dopa, to a patient suffering from Parkinson's disease is particularly beneficial. Remacemide, or a pharmaceutically acceptable salt thereof, may also be useful in the treatment of Parkinson's disease on its own.

Thus, according to the present invention, there is provided:

the use of remacemide, or a pharmaceutically acceptable salt thereof, as active ingredient in the manufacture of a medicament for the treatment of Parkinson's disease: and a pharmaceutical product containing remacemide or a pharmaceutically acceptable salt thereof, and L-dopa, as a combined preparation for separate, simultaneous or sequential use in the treatment of Parkinson's disease.

The administration of the active agents (ie remacemide, or a pharmaceutically acceptable salt thereof, and L-dopa) in conjunction with one another is advantageous because, for example, the therapeutic effect of L-dopa is particularly enhanced, permitting the therapeutic effect of L-dopa to be achieved at a dosage level below that normally employed, thus allowing the unwanted side effects of L-dopa (for example neurotoxicity) to be eliminated or substantially mitigated.

Pharmaceutically acceptable salts of remacemide include acid addition salts, for example the hydrochloride and hydrobromide salts.

By "simultaneous use" is meant administration of the two active agents in a single pharmaceutical formulation. Thus, according to a further aspect of the invention, there is provided a pharmaceutical formulation comprising remacemide or a pharmaceutically acceptable salt thereof, L-dopa, and a pharmaceutically acceptable adjuvant, diluent or carrier.

By "sequential use" is meant administration of the two active agents in separate pharmaceutical formulations, but with a short period of time between each administration, for example up to 5 minutes. By "separate use" is meant administration of the two active agents in separate pharmaceutical formulations, but with a relatively longer period of time between each administration, for example from 5 minutes to 12 hours.

The active agents may be administered by any convenient route, for example parentally, rectally, and of particular interest - orally. Pharmaceutical formulations comprising the active agents include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid compositions may be prepared by mixing the active agents with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation composition in which the active agents are uniformly dispersed. The solid dosage forms may be coated or otherwise compounded to prolong the action of the composition.

According to a further aspect of the invention, there is provided a method of treatment of Parkinson's disease, which comprises administering, separately, simultaneously or sequentially, remacemide or a pharmaceutically acceptable salt thereof, and L-dopa, in amounts which together are therapeutically effective, to a patient suffering from the disease.

In general, in humans, a total oral daily dose of from about 150–800 mg of L-dopa, in conjunction with from 50 to 300mg of remacemide or a pharmaceutically acceptable salt thereof, is suitable. The daily dose of each agent may be divided into, for example, up to 4 smaller amounts to be taken during the course of each day.

Thus, in the pharmaceutical products, formulations and method of treatment according to the invention, the active agents are preferably present or used in a w/w ratio of remacemide or a pharmaceutically acceptable salt thereof to L-dopa of from 1:2–1:4, for example 1:3.

The invention is illustrated by the following Example.

EXAMPLE

Male Sprague-Dawley rats (125–150 g) were rendered akinetic by administration of reserpine (so as to produce a monoamine depleted Parkinson's disease-like state, 5 mg/kg) 24 hours prior to testing. Motor activity was quantified using cages equipped with infra-red sensor beams. In rats treated with reserpine, L-Dopa increased horizontal locomotor activity in a dose-dependent fashion. When a sub-therapeutic dose of L-dopa (75 mg/kg, i.p.) was co-administered with remacemide (5–40 mg/kg, p.o.) there was a dose-dependent increase in horizontal locomotor activity.

In a comparison with the NMDA antagonist 10,11-dihydro-5-methyl-5H-dibenzo [a,d]-cyclohepten-5,10-imine (MK-801), remacemide was found to potentiate the effect of L-dopa over a broader dose range.

We claim:

1. A method of treatment of Parkinson's disease in a patient in need of such treatment, which method comprises the step of administering to said patient a therapeutically effective amount of remacemide or a pharmaceutically acceptable acid addition salt thereof.

* * * * *